(12) United States Patent
Dinsmore

(10) Patent No.: US 6,491,912 B2
(45) Date of Patent: *Dec. 10, 2002

(54) PORCINE CARDIOMYOCYTES AND THEIR USE IN TREATMENT OF INSUFFICIENT CARDIAC FUNCTION

(75) Inventor: Jonathan Dinsmore, Brookline, MA (US)

(73) Assignee: Diacrin, Inc., Charlestown, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/270,145

(22) Filed: Mar. 16, 1999

(65) Prior Publication Data

US 2001/0053354 A1 Dec. 20, 2001

Related U.S. Application Data

(63) Continuation of application No. 08/454,989, filed on May 30, 1995, now Pat. No. 5,919,449.

(51) Int. Cl.$^7$ ............................................... A01N 63/00

(52) U.S. Cl. ..................................... 424/93.7; 435/325

(58) Field of Search .......................... 424/93.7; 435/325

(56) References Cited

U.S. PATENT DOCUMENTS 5,283,058 A   2/1994   Faustman .................... 424/88

FOREIGN PATENT DOCUMENTS

| WO | WO 92/04033 | 3/1992 |
| WO | WO 95/14079 | 5/1995 |
| WO | WO 95/27042 | 10/1995 |
| WO | WO 95/33828 | 12/1995 |

OTHER PUBLICATIONS

Li et al., Circulation (Supplement), vol. 94, No. 8, Abstract 993, 1996.*
Leor J, et al. Transplantation of fetal myocardial tissue into the infarcted myocardium of rat. A potential method for repair of infarcted myocardium? Circulation. 1996 Nov. 1;94(9Suppl):II332–6.
Scorsin M, et al. Does transplantation of cardiomyocytes improve function of infarcted myocardium? Circulation. 1997 Nov. 4;96(9 Suppl):II–188–93.
Brauer, R.B. et al. (1993) "Use of C6–Deficient Rats to Evaluate the Mechanism of Hyperacute Rejection of Discordant Cardiac Xenografts", J. Immunol. 151(12):7240–7248.
Crombleholme, Timothy M. et al. (1991) "Transplantation of Fetal Cells" Am J. Obstet Gynecol, vol. 164, No. 1, Part 1, pp. 218–230.

DeBault, L. et al. (1992) "Ultrastructural Features in Hyperacutely Rejected Baboon Cardiac Allografts and Pig Cardiac Xenografts" Transplant. Proc. 24(2):612–613.
Delcarpio, Joseph B. et al. (1995) "Cardiomyocyte Transfer Into The Mammalian Heart" Annals of The New York Academy of Sciences, vol. 752, pp. 267–287.
Dinsmore et al. (1994) "Isolation, Growth, Differentiation, And Transplantation of Pig Fetal Pancreatic Cells" Molecular Biology of the Cell 5:350A (abstract 2032).
Faustman, D. and C. Coe (1991) "Prevention of Xenograft Rejection by Masking Donor HLA Class I Antigens" Science 252:1700–1702.
Faustman, D. and C. Coe (1992) "Xenograft Acceptance by Masking Donor Antigens" Transplant. Proc. 24(6):2854–2855.
Fischel, F.J. et al. (1991) "Cardiac Xenografting in the Pig to Rhesus Model: Manipulation of Anti–Endothelial AB Prolongs Survival" J. Heart and Lung Transplant. 10(1 Part 2): 170 (Abstract No. 67).
Gordon, Helmut A. (1971) "The Gnotobiotic Animal As A Tool In The Study of Host microbial Relationships" Bacterological Reviews, vol. 35, No. 4, pp. 390–429.
Hirata, A.A. and P. I. Terasaki (1972) "Masking of Human Transplantation Antigens by Divers Substances" J. Immunol. 108(6):1542–1550.
Isobe, M. et al. (1992) "Specific Acceptance of Cardiac Allograft After Treatment with Antibodies to ICAM–1 and LFA–1" Science 255:1125–1127.
Jendrisak, M. et al. (1993) "Prolongation in Murine Cardiac Allograft Survival With Monoclonal Antibodies to LFA–1, ICAM–1, CD4" Transplant. Proc. 25(1):825–827.

(List continued on next page.)

Primary Examiner—Patrick J. Nolan
(74) Attorney, Agent, or Firm—Lahive & Cockfield, LLP; Giulio A. DeConti, Jr., Esq.; Amy E. Mandragouras, Esq.

(57) ABSTRACT

Porcine cardiomyocytes and methods for using the cardiomyocytes to treat disorders characterized by insufficient cardiac function are described. The porcine cardiomyocytes are preferably embryonic porcine cardiomyocytes. The porcine cardiomyocytes can be modified to be suitable for transplantation into a xenogeneic subject, such as a human. For example, the porcine cardiomyocytes can be modified such that an antigen (e.g., an MHC class I antigen) on the cardiomyocyte surface which is capable of stimulating an immune response against the cardiomyocytes in a xenogeneic subject is altered (e.g., by contact with an anti-MHC class I antibody, or a fragment or derivative thereof) to inhibit rejection of the cardiomyocyte when introduced into the subject. In one embodiment, the porcine cardiomyocytes are obtained from a pig which is essentially free from organisms or substances which are capable of transmitting infection or disease to the recipient subject. The porcine cardiomyocytes of the present invention can be used to treat disorders characterized by insufficient cardiac function, e.g., congestive heart failure, in a xenogeneic subject by administering the cardiomyocytes to the subject.

9 Claims, 2 Drawing Sheets

OTHER PUBLICATIONS

Kaplon, R.J. et al. (1993) "Prolonged Survival of Neonatal Pig to Baboon Cardiac Xenografts" *Circulation* 88(4 Part 2):140 (Abstract No. 0202).

Kaplon, R.J. et al. (1994) "Prolonged Survival of Pig Cardiac Xenografts in Unmodified Newborn Baboons" *Transplant. Proc.* 26(3):1072.

Kawauchi, M. et al. (1994) "Cardiac Xenotransplantation From Pig to Japanese Monkey With Splenectomy, Tacrolims, Filtration Plasmapheresis, and Nafamstat Mesilate" *Transplant. Proc.* 26(3):1076–1077.

Kobayashi, T. et al. (1995) "Prolongation of Graft Survival Following Pit–to–Baboon Heart Transplantation by Cobra Venom Factor (CVF) Without Natural Antibody Depletion" *J. Heart and Lung Transplant.* 14(1 Part 2):S72 (Abstract No. 148a).

Koh, G.Y. et al. (1993) "Long–term survival of AT–1 cardiomyocyte grafts in syngenic myocardium" *Am. J. Physiol.* 264:H1727–H1733.

Leventhal, J.R. et al. (1992) "Evidence that 15–Deoxyspergualin Inhibits Natural Antibody Production But Fails to Prevent Hyperacute Rejection in a Discordant Xenograft Model" *Transplantation* 54(1):26–31.

Lie, W.R. et al. (1988) "Preparation and Characterization of Murine Monoclonal Antibodies to Swine Lymphocyte Antigens" *Immunology* 64:599–605.

Michler, R.E. et al. (1994) "Prolonged Survival of Porcine Cardiac Xenografts in Unmanipulated Newborn Baboon" *J. Heart and Lung Transplant.* 13(1 Part 2):S88 (Abstract No. 225).

Nowak, R. (1994) "New Cell Transplants May Mend a Broken Heart" *Science* 264:31.

Oettinger, H.F. et al. (1995) "Porcine Repeat Element DNA: In Situ Detection of Xenotransplanted Cells" *Cell Transplantation* 4(2):253–256.

Oriol, R. et al. (1993) "Carbohydrate Antigens of Pig Tissues Reacting with Human Natural Antibodies as Potential Targets for Hyperacute Vascular Rejection in Pid–to–Man Organ Xenotransplantation" *Transplantation* 56(6):1433–1442.

Osorio, R.W. et al. (1994) "Prolongation of in vivo Mouse Islet Allograft Survival by Modulation of MHC Class I Antigen" *Transplantation* 57(6):783–788.

Pruitt, S.K. et al. (1994) "The Effect of Soluble Complement Receptor Type 1 on Hyperacute Rejection of Porcine Xenografts" *Transplantation* 57(3):363–370.

Rajasinghe, Hiranya A. et al. (1996) "Early Fetal Exposure to Xenogeneic Donor Cardiac Myocytes and Postnatal Xenografting in an Ovine Model" Supplement to Circulation, vol. 94, No. 8, Abstract 0096.

Roark, J.H. et al. (1992) "Prolongation of Rat Pancreatic Islet Allograft Survival by Anti–$CD_2$ Monoclonal Antibody Treatment" *Transplantation* 54(6):1098–1103.

Rojansky, N. and Schenker, J.G. (1993) "The Use of Fetal Tissue For Therapeutic Applications" Int J. Gynecol Obstet, vol. 41, pp. 233–240.

Simon, A. et al. (1991) "Characterisation of human cardiac valve endothelium and porcine xenografts" *Immunobiology* 183(3–4):276 (Abstract No. M.17).

Soonpaa, M.H. et al. (1994) "Formation of Nascent Intercalated Disks Between Grafted Fetal Cardiomyocytes and Host Myocardium" *Science* 264:98–101.

Spinale, Francis G. et al. (1993) "Contractile Properties Of Isolated porcine Ventricular Myoctes" Cardiovascular Research, vol. 27(2), pp. 304–311.

Van Meter et al. (1995) "Myoblast Transplantation in the Porcine Model: A Potential Technique for Myocardial Repair" *Journal of Thoracic and Cardiovascular Surgery* 110(5):1442–1448.

Hertel–Wulff et al. (1994) "Long Term Survival of Pancreatic islets In Diabetic Monkeys" *Cell Transplantation* 3(3):216 (abstract 20).

Yatschoff, R. et al. (1993) "Efficacy of Rapamycin and RS–61443 in the Prolongation of Survival of Discordant Pig to Rabbit Cardiac Xenografts" *Clinical and Investigative Medicine* 16(4 Suppl.):B137 (Abstract No. 851).

Zashikhin, A.L. (1978) "Quantitative Study of Intranuclear DNA In Conductive Myocytes And Myocardial Contractile Cells In Some Stages of Embryogenesis" Krovoobrashshchenie, vol. 11, pp. 8–10.

Zehr, K.J. et al. (1994) "Neutrophil Adhesion and Complement Inhibition Prolongs Survival of Cardiac Xenografts in Discordant Species" *Transplantation* 57(6):900–906.

\* cited by examiner

PORCINE CARDIOMYOCYTES AND THEIR USE IN TREATMENT OF INSUFFICIENT CARDIAC FUNCTION

RELATED APPLICATIONS

This application is a continuation of U.S. Ser. No. 08/454,989, filed on May 30, 1995, now issued as U.S. Pat. No. 5,919,449, which is incorporated herein in its entirety by this reference.

BACKGROUND OF THE INVENTION

Heart disease is the predominant cause of disability and death in all industrialized nations. In the United States, it accounts for about 335 deaths per 100,000 individuals (approximately 40% of the total mortality) overshadowing cancer, which follows with 183 deaths per 100,000 individuals. Four categories of heart disease account for about 85–90% of all cardiac-related deaths. These categories include: ischemic heart disease, hypertensive heart disease and pulmonary hypertensive heart disease, valvular disease, and congenital heart disease. Ischemic heart disease, in its various forms, accounts for about 60–75% of all deaths caused by heart disease. One of the factors that renders ischemic heart disease so devastating is the inability of the cardiac muscle cells to divide and repopulate areas of ischemic heart damage. As a result, cardiac cell loss as a result of injury or disease is irreversible.

Human to human heart transplants have become the most effective form of therapy for severe heart damage. Many transplant centers now have one-year survival rates exceeding 80–90% and five-year survival rates above 70% after cardiac transplantation. Infections, hypertension, and renal dysfunction caused by cyclosporin, rapidly progressive coronary atherosclerosis, and inmunosuppressant-related cancers have been major complications however. Heart transplantation, moreover, is limited by the scarcity of suitable donor organs. In addition to the difficulty in obtaining donor organs, the expense of heart transplantation prohibits its widespread application. Another unsolved problem is graft rejection. Foreign hearts and heart cells are poorly tolerated by the recipient and are rapidly destroyed by the immune system in the absence of immunosuppressive drugs. While immunosuppressive drugs may be used to prevent rejection, they also block desirable immune responses such as those against bacterial and viral infections, thereby placing the recipient at risk of infection. There is a clear need, therefore, to address the limitations of the current heart transplantation therapy as treatment for heart disease.

SUMMARY OF THE INVENTION

To overcome the current limitations of whole heart transplantation to treat heart disorders, the present invention provides cardiomyocytes, compositions including the cardiomyocytes, and methods for treating disorders characterized by insufficient cardiac function by administering the cardiomyocytes to subjects with such disorders. The cardiomyocytes of the present invention offer several advantages over whole heart transplantation to treat cardiac disorders. The cardiomyocytes are isolated from pigs, which provide a convenient, relatively inexpensive, and abundant source of cardiomyocytes. Moreover, in some instances, the cardiomyocytes of the invention can be modified such that rejection of the cardiomyocytes upon introduction into a xenogeneic recipient is inhibited, thereby eliminating the requirement for generalized suppression of the immune system.

Accordingly, the present invention pertains to an isolated porcine cardiomyocyte or an isolated population of porcine cardiomyocytes suitable for transplantation into a xenogeneic subject, particularly a human subject. In a preferred embodiment, the xenogeneic subject has a disorder characterized by insufficient cardiac function. Examples of such disorders include ischemic heart disease, hypertensive heart disease and pulmonary hypertensive heart disease (cor pulmonale), valvular disease, congenital heart disease, and any condition which leads to congestive heart failure. The porcine cardiomyocyte(s), in unmodified form, has at least one antigen on the cell surface which is capable of stimulating an immune response against the cardiomyocyte in a xenogeneic subject, for example, a human. The antigen on the surface of the porcine cardiomyocyte is altered to inhibit rejection of the cardiomyocyte when introduced into a xenogeneic subject. In one embodiment, the cardiomyocyte surface antigen which is altered is an MHC class I antigen. This MHC class I antigen can be contacted, prior to transplantation into a xenogeneic subject, with at least one anti-MHC class I antibody, or a fragment or derivative thereof, which binds to the MHC class I antigen on the cardiomyocyte surface but does not activate complement or induce lysis of the cardiomyocyte. One example of an anti-MHC class I antibody is an anti-MHC class I $F(ab')_2$ fragment, such as an anti-MHC class I $F(ab')_2$ fragment of a monoclonal antibody PT85. The present invention also pertains to compositions which include porcine cardiomyocytes and antibodies, antibody fragments, or derivatives, which bind an antigen on the surface of the porcine cardiomyocytes. These compositions can be inserted into a delivery device, e.g., a syringe, which facilitates the introduction of the cardiomyocytes into a subject. In addition, the porcine cardiomyocytes of the invention can be grown as a cell culture in a medium suitable to support the growth of the cells. In one embodiment, the cell culture includes a population of porcine cardiomyocytes in which at least about 30% of the cardiomyocytes express cardiac troponin and/or myosin. In another embodiment, the cell culture includes a population of porcine cardiomyocytes which contract synchronously.

Porcine cardiomyocytes which are suitable for transplantation into a xenogeneic subject can be obtained from both embryonic (i.e., fetal), newborn, and adult pigs. Preferred porcine cardiomyocytes are embryonic porcine cardiomyocytes obtained from an embryonic pig at a selected gestational age. The preferred gestational age of embryonic pigs from which to obtain cardiomyocytes suitable for transplantation into xenogeneic subjects, particularly humans, is between about day twenty (20) and birth of the pig. In other preferred embodiments, the cardiomyocytes are isolated between about day twenty (20) and about day eighty (80), more preferably between about day twenty (20) and about day sixty (60), yet more preferably between about day twenty (20) and about day fifty (50), still more preferably between about twenty (20) and about day forty (40), still further preferably between about day twenty (20) and about day thirty (30), and most preferably between about day twenty-five (25) and about day twenty-eight (28) of gestation.

The invention further pertains to an isolated porcine cardiomyocyte or an isolated population of cardiomyocytes obtained from a pig which is essentially free from organisms which are capable of transmitting infection or disease to a xenogeneic recipient, e.g., a human. Categories of pathogens from which the pig is free can include parasites, bacteria, mycoplasma, and viruses. In one embodiment, the pig from which the cardiomyocytes are isolated is free of the following organisms: Toxoplasma, eperythrozoon, brucella, listeria, mycobacterium TB, leptospirillum, haemophilus suis, M. Hyopneumonia, porcine respiratory reproductive syndrome, rabies, pseudorabies, parvovirus, encephalomyocarditus virus, swine vesicular disease, techen (Porcine polio virus), hemagglutinating encephalomyocarditus, suipoxvirus, swine influenza type A, adenovirus, transmissible gastroenteritis virus, bovine viral diarrhea, and vesicular stomatitis virus. The cardiomyocytes obtained from pathogen-free pigs can be modified as described herein to inhibit rejection of the cardiomyocytes upon introduction into a xenogeneic subject. Preferred cardiomyocyte ages are also described herein. The present invention also pertains to compositions which include porcine cardiomyocytes obtained from pathogen-free pigs and antibodies, antibody fragments, or derivatives, which bind an antigen on the surface of the porcine cardiomyocytes. These compositions can also be inserted into a delivery device, e.g., a syringe, which facilitates the introduction of the cardiomyocytes into a subject. In addition, the porcine cardiomyocytes obtained from pathogen-free pigs can be grown as a cell culture in a medium suitable to support the growth of the cells. In one embodiment, the cell culture includes a population of porcine cardiomyocytes in which at least about 30% of the cardiomyocytes express cardiac troponin and/or myosin. In another embodiment, the cell culture includes a population of porcine cardiomyocytes which contract synchronously.

Another aspect of the invention pertains to methods for treating disorders characterized by insufficient cardiac function, e.g., such as ischemic heart disease, hypertensive heart disease and pulmonary hypertensive heart disease (cor pulmonale), valvular disease, congenital heart disease, and any condition which leads to congestive heart failure, in a subject, particularly a human subject. These methods include administering to a subject having such a disorder, porcine cardiomyocytes of the present invention. In one embodiment, the porcine cardiomyocytes which can be administered to a subject having a cardiac disorder are porcine cardiomyocytes which, in unmodified form, have at least one antigen on the surface of the cardiomyocytes which is capable of stimulating an immune response against the cardiomyocytes in a xenogeneic subject, for example, a human. The antigen on the surface of the porcine cardiomyocytes is altered to inhibit rejection of the cardiomyocytes when introduced into a xenogeneic subject. Examples of cardiomyocyte surface antigens and methods of altering such antigens are described herein. Preferred cardiomyocyte ages are also described herein. In another embodiment, the porcine cardiomyocytes which can be administered to a subject having a disorder characterized by insufficient cardiac function are porcine cardiomyocytes which are obtained from a pig which is essentially free from organisms which are capable of transmitting infection or disease to a xenogeneic recipient, e.g., a human, of the cardiomyocytes. Pathogen-free pigs are described in detail herein. These cardiomyocytes can also be modified as described herein. Transplantation of the porcine cardiomyocytes can be accompanied by administration of an immunosuppressive agent, e.g., cyclosporin A, FK506, RS-61443, or a T cell antibody, to the subject.

DETAILED DESCRIPTION OF THE INVENTION

Figure 1A:
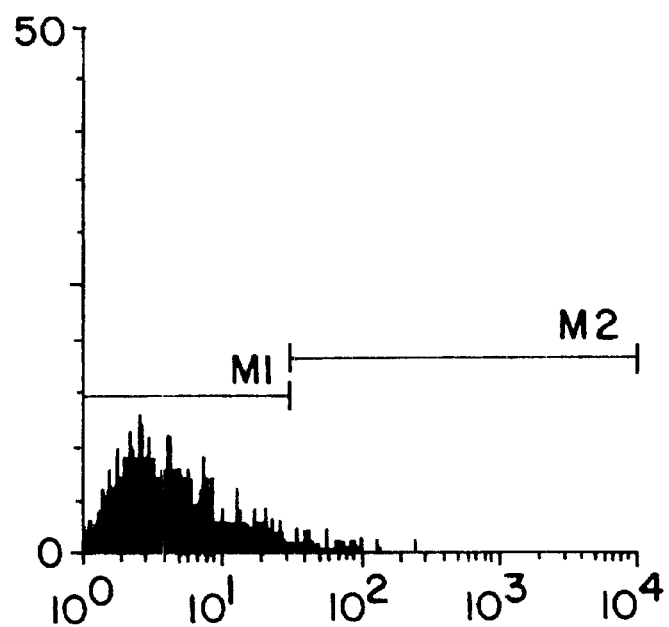
FIGS. 1A–1B are FACS analyses of isolated porcine cardiomyocytes incubated with a primary mouse monoclonal antibody to cardiac troponin and a goat anti-mouse fluorescein conjugated secondary antibody (FIG. 1B) or incubated with the secondary antibody alone (control) (FIG. 1A).
Figure 1B:
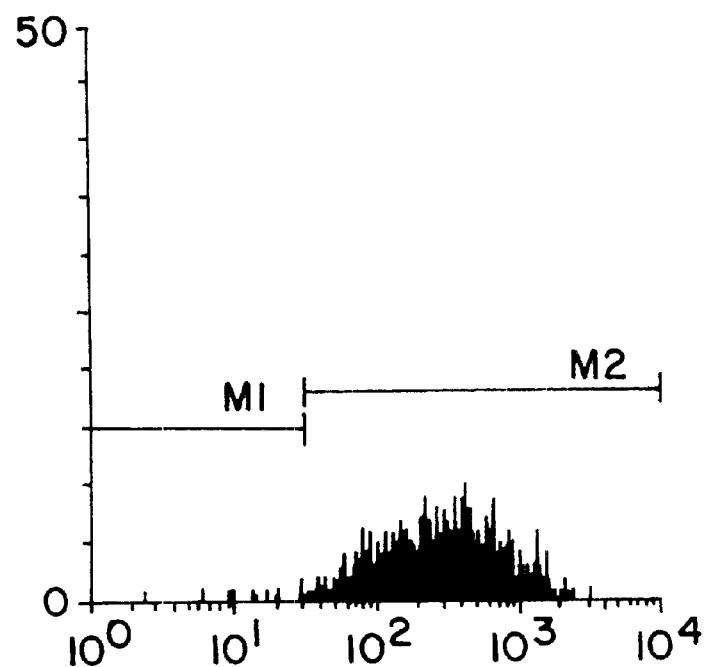

I. Isolated Cells and Cell Population of the Invention

A. Porcine Cardiomyocytes of the Invention

The invention features an isolated porcine cardiomyocyte and isolated populations of porcine cardiomyocytes suitable for introduction into a xenogeneic recipient. These cells can be used to treat disorders, such as ischemic heart disease, hypertensive heart disease and pulmonary hypertensive heart disease (cor pulmonale), valvular disease, congenital heart disease, and any condition which leads to congestive heart failure, which are characterized by insufficient cardiac function. As used herein, the term "isolated" refers to a cell which has been separated from its natural environment. This term includes gross physical separation from its natural environment, e.g., removal from the donor animal, e.g., a pig, and alteration of the cell's relationship with the neighboring cells with which it is in direct contact by, for example, dissociation. The term "isolated" does not refer to a cell which is in a tissue section, is cultured as part of a tissue section, or is transplanted in the form of a tissue section. When used to refer to a population of porcine cardiomyocytes, the term "isolated" includes populations of cells which result from proliferation of the isolated cells of the invention. As used herein, the term "porcine" is used interchangeably with the terms "pig" and "swine" and refers to mammals in the family Suidae. Such mammals include wholly or partially inbred swine, e.g., miniature swine, and transgenic swine. The terms "cardiomyocyte" and "cardiac muscle cell" are used interchangeably herein and refer to a cell which is involved in a normal cardiac function. For example, a normal cardiac function is contraction. The cardiac muscle cells are the individual contracting units of the heart. Synchronous contraction of the cardiac muscle cells results in heart beats.

Cardiomyocytes of the invention are obtained from the heart of a donor swine such as, for example, a swine which is essentially pathogen-free as described herein. In a preferred embodiment, the cardiomyocytes are obtained from the embryonic swine heart at a selected gestational age. The selected gestational ages (the total gestation time for pig is approximately 115 days) for obtaining embryonic cardiomyocytes can be determined, for example, based on the following criteria: the viability of the cells upon isolation from the donor pig, the ability of the cells to divide, for example, in culture; the ability of the cells to express protein or peptide associated with normal cardiac morphology and/or function (e.g., express cardiac-specific products such as cardiac troponin, myosin, actin, $Na^+/K^+$ATPase, and atrial natriuretic protein; the ability of the cells to contract; the ability of the cells to form junctions, e.g., gap junctions, with other cells; and the ability of the cells to respond to chronotropic agents, e.g., carbachol (a cholinergic agonist) and isoproterenol (a β-adrenergic agonist). The preferred gestational age of embryonic swine from which to obtain cardiomyocytes suitable for introduction into xenogeneic subjects, particularly humans, is between about day twenty (20) and birth of the pig. In other preferred embodiments, the cardiomyocytes are isolated between about day twenty (20) and about day eighty (80), more preferably between about day twenty (20) and about day sixty (60), yet more preferably between about day twenty (20) and about day fifty (50), still more preferably between about day twenty (20) and about day forty (40), still further preferably between about day twenty (20) and about day thirty (30), and most preferably between about day twenty-five (25) and about day twenty-eight (28) of gestation. As the embryonic pig nears the end of its gestation period, the developing heart becomes increasingly vascularized. The increasing amounts of vasculature results in an increased amount of endothelial cells which serve to dilute the potential number of cardiomyocytes which can be isolated from the heart. Moreover, it becomes more difficult to dissociate the cardiomyocytes from the increasing amounts of connective tissue as the fetus nears birth. Consequently, it is preferred that the age range for isolation of porcine cardiomyocytes is during the first half of gestation, i.e., during the first sixty (60) days of gestation.

When isolated from a donor swine, the cardiomyocytes of the invention are capable of, among other functions, dividing, expressing proteins normally expressed, e.g., troponin and myosin, by functional cardiomyocytes, and contracting. Cardiomyocytes within the preferred embryonic age range have some or all of the following characteristics: the cells form a monolayer of adherent cells (i.e., they adhere to culture substrate, e.g., culture dish, forming fibroblast-like cells); the cells are uniform in morphology, e.g., there are few if any contaminating cells (e.g., endothelial cells or connective tissue cells) and stain positive for cardiac troponin and myosin; the cells are capable of proliferating; and the cells can be maintained (i.e., remain viable) in culture for an extended period of time under appropriate conditions, e.g., several months, in a growth medium, and the cells can contract synchronously.

The present invention also features a population (i.e., a group of two or more cells) of porcine cardiomyocytes. The populations of cardiomyocytes of the invention can be grown as a cell culture, i.e., as a population of cells which grow in vitro, in a medium suitable to support the growth of the cells, e.g., prior to administration to a subject. The characteristics of the cells when grown as cell cultures are described herein in detail. Media which can be used to support the growth of porcine cardiomyocytes include mammalian cell culture media, such as those produced by Gibco BRL (Gaithersburg, MD). See 1994 Gibco BRL Catalogue & Reference Guide. The medium can be serum-free but is preferably supplemented with animal serum such as fetal calf serum. A preferred growth medium for the cardiomyocytes is MCDB 120+dexamethasone, e.g., 0.39 µg/ml,+ Epidermal Growth Factor (EGF), e.g., 10 ng/ml, +fetal caif serum, e.g., 15%. A preferred medium for cardiomyocyte maintenance is DMEM supplemented with horse serum, e.g., 10% horse serum. When isolated from a donor pig and/or when grown in culture, preferably at least about 20%, more preferably at least about 30%, yet more preferably at least about 40%, still more preferably at least about 50%, and most preferably at least about 60% or more of the cardiomyocytes express cardiac troponin and/or myosin, among other cardiac-specific cell products.

The cardiomyocytes of the invention can further be included in compositions. For example, such compositions can include antibodies, antibody fragments, or derivatives, which bind to at least one antigen on the cardiomyocyte surface which is capable of stimulating an immune response against the cardiomyocyte in a xenogeneic subject. Cardiomyocyte surface antigens are described in detail herein. In one embodiment, the compositions can also include a pharmaceutically acceptable carrier or diluent as described herein.

Cardiomyocytes of the invention can also be "modified to express a gene product". As used herein, the term "modified to express a gene product" is intended to mean that the cell is treated in a manner that results in the production of a gene product by the cell. Preferably, the cell does not express the gene product prior to modification. Alternatively, modification of the cell may result in an increased production of a gene product already expressed by the cell or result in production of a gene product (e.g., an antisense RNA molecule) which decreases production of another, undesirable gene product normally expressed by the cell.

In a preferred embodiment, a cell is modified to express a gene product by introducing genetic material, such as a nucleic acid molecule (e.g., RNA or, more preferably, DNA) into the cell. The nucleic acid molecule introduced into the cell encodes a gene product to be expressed by the cell. The term "gene product" as used herein is intended to include proteins, peptides and functional RNA molecules. Generally, the gene product encoded by the nucleic acid molecule is the desired gene product to be supplied to a subject. Alternatively, the encoded gene product is one which induces the expression of the desired gene product by the cell (e.g., the introduced genetic material encodes a transcription factor which induces the transcription of the gene product to be supplied to the subject). Examples of gene products that can be delivered to a subject via a genetically modified cardiomyocyte include gene products that can prevent future cardiac disorders, such as growth factors which encourage blood vessels to invade the heart muscle, e.g., Fibroblast Growth Factor (FGF) 1, FGF-2, Transforming Growth Factor β (TGF-β), and angiotensin. Other gene products that can be delivered to a subject via a genetically modified cardiomyocyte include factors which promote cardiomyocyte survival, such as FGF, TGF-β, IL-10, CTLA 4-Ig, and bcl-2.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene product encoded by the gene. Regulatory sequences which can be included in the nucleic acid molecule include promoters, enhancers and polyadenylation signals, as well as sequences necessary for transport of an encoded protein or peptide, for example N-terminal signal sequences for transport of proteins or peptides to the surface of the cell or for secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements which are known in the art include upstream regions from the dystrophin gene (Klamut et al., (1989) *Mol. Cell. Biol.* 9:2396), the creatine kinase gene (Buskin and Hauschka, (1989) *Mol. Cell Biol.* 9:2627) and the troponin gene (Mar and Ordahl, (1988) *Proc. Natl. Acad. Sci. USA.* 85:6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S. and White, J. H. (1993) *Proc. Natl. Acad Sci. USA* 90:5603–5607), synthetic ligand-regulated elements (see, e.g. Spencer, D. M. et al. (1993) *Science* 262:1019–1024) and ionizing radiation-regulated elements (e.g., see Manome, Y. et al. (1993) *Biochemistry* 32:10607–10613; Datta, R. et al. (1992) *Proc. Natl. Acad. Sci. USA* 89:10149–10153). Additional tissue-specific or inducible regulatory systems which may be developed can also be used in accordance with the invention.

There are a number of techniques known in the art for introducing genetic material into a cell that can be applied to modify a cell of the invention. In one embodiment, the nucleic acid is in the form of a naked nucleic acid molecule. In this situation, the nucleic acid molecule introduced into a cell to be modified consists only of the nucleic acid encoding the gene product and the necessary regulatory elements. Alternatively, the nucleic acid encoding the gene product (including the necessary regulatory elements) is contained within a plasmid vector. Examples of plasmid expression vectors include CDM8 (Seed, B. (1987) *Nature* 329:840) and pMT2PC (Kaufman, et al. (1987) *EMBO J.* 6:187–195). In another embodiment, the nucleic acid molecule to be introduced into a cell is contained within a viral vector. In this situation, the nucleic acid encoding the gene product is inserted into the viral genome (or a partial viral genome). The regulatory elements directing the expression of the gene product can be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells. or by incubating the cells and the DNA together in an appropriate buffer and subjecting the cells to a high-voltage electric pulse (i.e., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection. For an in vitro culture of cells, DNA can be introduced by microinjection in vitro or by a gene gun in vivo.

Alternatively, naked DNA can also be introduced into cells by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. An alternative method for generating a cell that is modified to express a gene product involving introducing naked DNA into cells is to create a transgenic animal which contains cells modified to express the gene product of interest.

Use of viral vectors containing nucleic acid, e.g., a cDNA encoding a gene product, is a preferred approach for introducing nucleic acid into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for a review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques.

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:3239; Tratschin et al. (1984) *J. Virol.* 51:611–619; and Flotte et al. (1993) *J. Biol. Chem.* 268:3781–3790).

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells which efficiently express the gene product. Such a population of uniform cells can be prepared by isolating a single modified cell by limiting dilution cloning followed by expanding the single cell in culture into a clonal population of cells by standard techniques.

Alternative to introducing a nucleic acid molecule into a cell to modify the cell to express a gene product, a cell can be modified by inducing or increasing the level of expression of the gene product by a cell. For example, a cell may be capable of expressing a particular gene product but fails to do so without additional treatment of the cell. Similarly, the cell may express insufficient amounts of the gene product for the desired purpose. Thus, an agent which stimulates expression of a gene product can be used to induce or increase expression of a gene product by the cell. For example, cells can be contacted with an agent in vitro in a culture medium. The agent which stimulates expression of a gene product may function, for instance, by increasing transcription of the gene encoding the product, by increasing the rate of translation or stability (e.g., a post transcriptional modification such as a poly A tail) of an mRNA encoding the product or by increasing stability, transport or localization of the gene product. Examples of agents which can be used to induce expression of a gene product include cytokines and growth factors.

Another type of agent which can be used to induce or increase expression of a gene product by a cell is a transcription factor which upregulates transcription of the gene encoding the product. A transcription factor which upregulates the expression of a gene encoding a gene product of interest can be provided to a cell, for example, by introducing into the cell a nucleic acid molecule encoding the transcription factor. Thus, this approach represents an alternative type of nucleic acid molecule which can be introduced into the cell (for example by one of the previously discussed methods). In this case, the introduced nucleic acid does not directly encode the gene product of interest but rather causes production of the gene product by the cell indirectly by inducing expression of the gene product.

B. Modified Porcine Cardiomyocytes and an Isolated Population of Modified Porcine Cardiomyocytes A further aspect of the invention is a porcine cardiomyocyte and an isolated population of porcine cardiomyocytes in which the cardiomyocyte(s), in unmodified form, has at least one antigen on its surface which is capable of stimulating an immune response against the cardiomyocyte in a xenogeneic subject. To inhibit rejection of the cardiomyocyte when introduced into the xenogeneic subject, the antigen on the cardiomyocyte surface is altered prior to transplantation. In an unaltered state, the antigen on the cardiomyocyte surface stimulates an immune response against the cardiomyocyte when the cardiomyocyte is administered to a subject (also referred to herein as recipient or recipient subject). By altering the antigen, the normal immunological recognition of the porcine cardiomyocyte by the immune system cells of the recipient is disrupted and additionally, "abnormal" immunological recognition of this altered form of the antigen can lead to porcine cardiomyocyte-specific long term unresponsiveness in the recipient. It is likely that alteration of an antigen on the porcine cardiomyocyte prior to introducing the cardiomyocyte into a subject interferes with the initial phase of recognition of the porcine cardiomyocyte by the cells of the host's immune system subsequent to administration of the cardiomyocyte. Furthermore, alteration of the antigen may induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the term "altered" encompasses changes that are made to at least one porcine cardiomyocyte antigen(s) which reduces the immunogenicity of the antigen to thereby interfere with immunological recognition of the antigen(s) by the recipient's immune system.

Antigens to be altered according to the current invention include antigens on a porcine cardiomyocyte which can interact with an immune cell in a xenogeneic (or allogeneic) recipient subject and thereby stimulate a specific immune response against the porcine cardiomyocyte in the recipient. The interaction between the antigen and the immune cell may be an indirect interaction (e.g., mediated by soluble factors which induce a response in the immune cell, e.g., humoral mediated) or, preferably, is a direct interaction between the antigen and a molecule present on the surface of the immune cell (i.e., cell-cell mediated). As used herein, the term "immune cell" is intended to include a cell which plays a role in specific immunity (e.g., is involved in an immune response) or plays a role in natural immunity. Examples of immune cells include all distinct classes of lymphocytes (T lymphocytes, such as helper T cells and cytotoxic T cells, B lymphocytes, and natural killer cells), monocytes, macrophages, other antigen presenting cells, dendritic cells, and leukocytes (e.g., neutrophils, eosinophils, and basophils). In a preferred embodiment, the antigen is one which interacts with a T lymphocyte in the recipient (e.g., the antigen normally binds to a receptor on the surface of a T lymphocyte).

In one embodiment, the antigen on the porcine cardiomyocyte to be altered is an MHC class I antigen. Alternatively, an adhesion molecule on the cardiomyocyte surface, such as NCAM-1 or ICAM-1, can be altered. An antigen which stimulates a cellular immune response against the cardiomyocyte, such as an MHC class I antigen, can be altered prior to transplantation by contacting the cardiomyocyte with a molecule which binds to the antigen. A preferred molecule for binding to the antigen is an antibody, or fragment thereof (e.g., an anti-MHC class I antibody, or fragment thereof, an anti-ICAM-1 antibody or fragment thereof, an anti-LFA-3 antibody or fragment thereof, or an anti-$\beta_2$ microglobulin antibody or fragment thereof). A preferred antibody fragment is an F(ab')$_2$ fragment. Polyclonal or, more preferably, monoclonal antibodies can be used. Other molecules which can be used to alter an antigen (e.g., an MHC class I antigen) include peptides and small organic molecules which bind to the antigen. Furthermore, two or more different epitopes on the same or different antigens on the cell surface can be altered. A particularly preferred monoclonal antibody for alteration of MHC class I antigens on porcine cardiomyocytes is PT85 (commercially available from Veterinary Medicine Research Development, Pullman Wash.). PT85 can be used alone to alter MHC class I antigens or, if each antibody is specific for a different epitope, PT85 can be used in combination with another antibody known to bind MHC class I antigens to alter the antigens on the cell surface. Suitable methods for altering a surface antigen on a cell for transplantation are described in greater detail in Faustman and Coe (1991) *Science* 252:1700–1702 and PCT publication WO 92/04033. Methods for altering multiple epitopes on a surface antigen on a cell for transplantation are described in greater detail in U.S. patent application Ser. No. 08/220,741, filed Mar. 31, 1994, the contents of which are incorporated herein by reference.

The altered (also referred to herein as "modified") porcine cardiomyocytes can comprise a population of cells. The modified or unmodified cells described herein can be grown as a cell culture, i.e., as a population of cells which grow in vitro, in a medium suitable to support the growth of the cells as described herein.

In another embodiment, the porcine cardiomyocytes of the present invention can be modified to inhibit natural antibody-mediated hyperacute rejection of the cells. For example, the cardiomyocytes of the invention may, in unmodified form, express an epitope on their surface which stimulates hyperacute rejection of the cardiomyocytes by natural antibodies in a recipient subject. Such an epitope can be altered, reduced or substantially eliminated. This treatment of the cardiomyocytes inhibits subsequent recognition of the epitope by natural antibodies in a recipient, thereby inhibiting hyperacute rejection. In a preferred embodiment, the epitope is a carbohydrate, preferably galactosyl($\alpha$1,3) galactose (Gal($\alpha$1,3)Gal). Dispersed cells can be treated or, alternatively, cells can be treated within a tissue or organ (e.g., liver).

Epitopes on the surface of the cardiomyocytes, in one embodiment of the invention, are removed from the surface of a cell, such as by enzymatic or chemical treatment of the cell. For example, Gal($\alpha$1,3)Gal epitopes can be cleaved from the cardiomyocyte surface by treatment of the cell with an alpha-galactosidase. In another embodiment, formation of the epitope on the cell surface is inhibited. This can be accomplished by inhibiting the activity of an enzyme which forms the epitope. For example, formation of Gal($\alpha$1,3)Gal epitopes on the surface of a cell can be interfered with by inhibiting the activity of an alpha-1,3-galactosyltransferase within the cell, such as by introducing into the cell a nucleic acid which is antisense to a coding or regulatory region of an alpha-1,3-galactosyltransferase gene or by treating the cell with a chemical inhibitor of the enzyme. In yet another embodiment, epitopes on a cardiomyocyte surface are altered by binding a molecule to the epitope, thereby inhibiting its subsequent recognition by natural antibodies in a recipient. For example, lectins, antibodies or antibody fragments can be bound to an epitope to inhibit its subsequent recognition by natural antibodies. Methods for altering epitopes on cell surfaces which stimulate hyperacute rejection of the cells by natural antibodies in a recipient subject are described in greater detail in U.S. patent application Ser. No. 08/253,782, filed Jun. 3, 1994, the contents of which are incorporated herein by reference.

C. Porcine Cardiomyocytes and Isolated Populations of Porcine Cardiomyocytes Obtained from Essentially Pathogen-Free Swine The invention also features a porcine cardiomyocyte and a population of porcine cardiomyocytes isolated from a swine which is essentially free from organisms or substances which are capable of transmitting infection or disease to a xenogeneic recipient, e.g., a human recipient, of the cells. Typically, porcine cardiomyocytes are isolated from a swine which is essentially free from human pathogens. For example, the pathogens from which the swine are free include, but are not limited to, one or more of pathogens from the following categories of pathogens: parasites, bacteria, mycoplasma, and viruses. The swine can be free from, for example, parasites such as toxoplasma and eperytherozoon, or mycoplasma, such as M. hyopneumonia. Examples of bacteria from which the swine can be free include brucella, listeria, mycobacterium TB, leptospirillum, and haemophilus suis. Additionally, the swine can be free from viruses such as zoonotic, cross placenta, and neurotropic viruses. Specific examples of viruses from which the swine are free include: a virus which causes (oi results in) porcine respiratory reproductive syndrome, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, cytomegalovirus, suipoxvirus, swine influenza type A, adenovirus, transmissible gastroenteritus virus, a virus which causes bovine viral diarrhea, parainfluenza virus 3, and vesicular stomatitis virus.

In one embodiment, the pigs from which cardiomyocytes are isolated are essentially free from one or more and preferably all of the following organisms: Toxoplasma, eperythrozoon, brucella, listeria, mycobacterium TB, leptospirillum, haemophilus suis, M. Hyopneumonia, a virus which causes porcine respiratory reproductive syndrome, a virus which causes rabies, a virus which causes pseudorabies, parvovirus, encephalomyocarditus virus, a virus which causes swine vesicular disease, porcine polio virus (techen), a virus which causes hemagglutinating encephalomyocarditus, suipoxvirus, swine influenza type A, adenovirus, transmissible gastroenteritis virus, a virus which causes bovine viral diarrhea, and vesicular stomatitis virus. The phrase "essentially free organism" (also referred to herein as "essentially pathogen-free") when referring to a swine from which cells are isolated means that the organism is not present in the swine in an amount which is capable of transmitting infection or disease to a xenogeneic recipient, e.g., a human. Example IV provides representative, but not limiting examples of methods for selecting swine which are essentially free from the various organisms. Embryonic, newborn, and adult swine which are determined to be essentially free of such organisms are maintained under suitable conditions until used as a source of cardiomyocytes.

Preferred gestational ages of the swine from which the cardiomyocytes of the invention are isolated are described in detail herein. Porcine cardiomyocytes isolated from essentially pathogen-free swine can additionally be modified to reduce the immunogenicity of the cells following transplantation into a xenogeneic subject as described herein.

II. Methods of the Invention

A. Methods for Treating Disorders Characterized by Insufficient Cardiac Function Using Porcine Cardiomyocytes A still further aspect of the invention pertains to methods for treating disorders characterized by insufficient cardiac function in a subject, e.g., a xenogeneic subject. These methods include administering to a xenogeneic subject having such a disorder porcine cardiomyocytes of the invention. Such porcine cardiomyocytes are described in detail in Section I above. The term "treating" as used herein includes reducing or alleviating at least one adverse effect or symptom of a disorder characterized by insufficient cardiac function. Adverse effects or symptoms of cardiac disorders are numerous and well characterized. Non-limiting examples of adverse effects or symptoms of cardiac disorders include: dyspnea, chest pain, palpitations, dizziness, syncope, edema, cyanosis, pallor, fatigue, and death. For additional examples of adverse effects or symptoms of a wide variety of cardiac disorders, see Robbins, S. L. et al. (1984) Pathological Basis of Disease (W. B. Saunders Company, Philadelphia) 547–609; Schroeder, S. A. et al. eds. (1992) Current Medical Diagnosis & Treatment (Appleton & Lange, Connecticut) 257–356. Transplantation of porcine cardiomyocytes of the invention into the heart of a human subject with a cardiac disorder results in replacement of lost cardiomyocytes. Porcine cardiomyocytes are introduced into a subject with a cardiac disorder in an amount suitable to replace lost cardiomyocytes such that there is an at least partial reduction or alleviation of at least one adverse effect or symptom of the cardiac disorder.

As used herein the terms "administering", "introducing", and "transplanting" are used interchangeably and refer to the placement of the porcine cardiomyocytes of the invention into a subject, e.g., a xenogeneic subject, by a method or route which results in localization of the cardiomyocytes at a desired site. The porcine cardiomyocytes can be administered to a subject by any appropriate route which results in delivery of the cells to a desired location in the subject where at least a portion of the cells remain viable. It is preferred that at least about 5%, preferably at least about 10%, more preferably at least about 20%, yet more preferably at least about 30%, still more preferably at least about 40%, and most preferably at least about 50% or more of the cells remain viable after administration into a subject. The period of viability of the cells after administration to a subject can be as short as a few hours, e.g., twenty-four hours, to a few days, to as long as a few weeks to months. One method that can be used to deliver the cardiomyocytes of the invention to a subject is direct injection of the cardiomyocytes into the ventricular myocardium of the subject. See e.g., Soonpaa, M. H. et al. (1994) *Science* 264:98–101; Koh, G. Y. et al. (1993) *Am. J. Physiol.* 33:H1727–1733. Cardiomyocyte can be administered in a physiologically compatible carrier, such as a buffered saline solution. To treat disorders characterized by insufficient cardiac function in a human subject, about $10^6$–$10^7$ pig cardiomyocytes can be introduced into the human, e.g., into the human heart. About $2$–$5 \times 10^4$ cardiomyocytes can be harvested from each fetal pig heart. Thus, about fifteen to about twenty fetal pigs (approximately one litter of a superovulated pregnant pig) are generally used to harvest the appropriate number of cells for introduction into a human subject. Moreover, as the cardiomyocytes of the invention undergo about six doublings in culture to yield an increased number of cells for transplantation, the number of pig fetuses needed for harvesting cardiomyocytes decreases.

To accomplish these methods of administration, the cardiomyocytes of the invention can be inserted into a delivery device which facilitates introduction by, injection or implantation, of the cardiomyocytes into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The porcine cardiomyocytes of the invention can be inserted into such a delivery device, e.g., a syringe, in different forms. For example, the cells can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating porcine cardiomyocytes as described herein in a pharmaceutically acceptable carrier or diluent and, as required, other ingredients enumerated above, followed by filtered sterilization.

Support matrices in which the porcine cardiomyocytes can be incorporated or embedded include matrices which are recipient-compatible and which degrade into products which are not harmful to the recipient. Natural and/or synthetic biodegradable matrices are examples of such matrices. Natural biodegradable matrices include, for example, collagen matrices. Synthetic biodegradable matrices include synthetic polymers such as polyanhydrides, polyorthoesters, and polylactic acid. These matrices provide support and protection for the cardiomyocytes in vivo.

The term "subject" is intended to include mammals, particularly humans, susceptible to diseases characterized by insufficient cardiac function. The term "subject" also includes mammals in which an immune response is elicited against allogeneic or xenogeneic cells. Examples of subjects include primates (e.g., humans, and monkeys). A "xenogeneic subject" (also referred to herein as "recipient subject" or "recipient") as used herein is a subject into which cells of another species are introduced or are to be introduced.

As used herein, the phrase "disorder characterized by insufficient cardiac function" includes an impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte or a population of cardiomyocytes. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, cardiomyopathy, cardiac disorders which result in congestive heart failure, and tumors of the heart, e.g., primary sarcomas and secondary tumors.

Prior to introduction into a subject, the porcine cardiomyocytes can be modified to inhibit immunological rejection. The porcine cardiomyocytes can, as described in detail herein, be rendered suitable for introduction into a xenogeneic subject by alteration of at least one immunogenic cell surface antigen (e.g., an MHC class I antigen). To inhibit rejection of transplanted porcine cardiomyocytes and to achieve immunological non-responsiveness in an allogeneic or xenogeneic transplant recipient, the method of the invention can include alteration of immunogenic antigens on the surface of the porcine cardiomyocytes prior to introduction into the subject. This step of altering one or more immunogenic antigens on porcine cardiomyocytes can be performed alone or in combination with administering to the subject an agent which inhibits T cell activity in the subject. Alternatively, inhibition of rejection of a porcine cardiomyocyte graft can be accomplished by administering to the subject an agent which inhibits T cell activity in the subject in the absence of prior alteration of an immunogenic antigen on the surface of the porcine cardiomyocytes. As used herein, an agent which inhibits T cell activity is defined as an agent which results in removal (e.g., sequestration) or destruction of T cells within a subject or inhibits T cell functions within the subject (i.e., T cells may still be present in the subject but are in a non-functional state, such that they are unable to proliferate or elicit or perform effector functions, e.g. cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunsuppressive drug is cyclosporin A. Other immunosuppressive drugs which can be used include FK506, and RS-61443. In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphosphamide). In another embodiment, an immunosuppressive drug is administered in conjunction with both a steroid and a chemotherapeutic agent. Suitable immunosuppressive drugs are commercially available (e.g., cyclosporin A is available from Sandoz, Corp., East Hanover, N.J.).

An immunsuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Kahan, B. D. (1989) *New Eng. J. Med.* 321(25):1725–1738). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the serum of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunsuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. (1991) *Transplantation* 52:545; Hutchinson et al. (1981) *Transplantation* 32:210; Green et al. (1979) *Lancet* 2:123; Hall et al. (1985) *J. Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with skin grafts by examining the transplanted tissue or by biopsy) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T celldepleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See U.S. patent application Ser. No.: 08/220,724, filed Mar. 31, 1994, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D. R. et al. (1991) *J. Immunol.* 147:3261–3267). Accordingly, an IL-2 or an IL-2 receptor antibody can be administered to a recipient to inhibit rejection of a transplanted cell (see e.g. Wood et al. (1992) *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of transplantation. The effectiveness of antibody treatment in depleting T cells from the peripheral blood can be determined by comparing T cell counts in blood samples taken from the subject before and after antibody treatment. Dosage regimes may be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example I
Isolation of Fetal Pig Cardiomyocytes

To stimulate superovulation, one Yorkshire gilt received PG-600®, a combination of Pregnant Mare's Serum Gonadotropin (PMSG) and human chorionic gonadotropin (HCG) used to stimulate the follicles of the ovaries to produce mature ova and to produce the outward signs of estrus. Three to five days from the time of administration of the PG-600®, the sows were observed for signs of estrus. Those gilts showing signs of estrus were then artificially inseminated. Twenty-four to twenty-eight days after insemination, one pregnant Yorkshire gilt (with a normal gestational period of 115 days) was euthanized by bolting. Uterine horns were removed and stored on ice for transport to a sterile laboratory facility (Diacrin, Inc., Charlestown, Mass.) where approximately 15–20 fetuses were delivered from the uterine pouch and transferred to sterile phosphate buffered saline (PBS).

The fetuses were removed from the storage dish containing PBS and placed in a sterile dissecting dish containing PBS. The dissecting dish was then placed on the stage of a dissecting microscope. With the aid of the dissecting microscope, a lateral incision along the ventral portion of the thoracic cavity of each fetus was made. The heart of the fetus was then exposed by pulling back the body wall laterally using watchmaker's forceps. Once the heart was exposed, it was removed with curved forceps by passing the forceps beneath the heart and gently pulling it free from its attachment to the vasculature.

The hearts were then transferred, using a large bore pipette, to a Petri dish containing a small volume (enough to keep tissue wet) of digestion buffer (0.05% trypsin, 0.05% collagenase P, 0.05% bovine serum albumin (BSA)). The hearts were cut into small pieces with a surgical blade and torn into fine pieces using the needles of two 1 cc syringes. Using a large bore pipette, tissue pieces were then transferred into a 50 ml conical tube and, together with additional volume, rinsed from the Petri dish, and spun down for 5 minutes at 200×g. Pelleted tissue was then resuspended in 0.4 ml of digestion buffer per heart and placed at 37° C. water bath with intermittent shaking. After 20 minutes of incubation, the digestion mixture was spun down for 5 minutes at 200×g and resuspended in the same volume of a fresh digestion buffer and returned for incubation for another 30 minutes Myocytes released into the medium after 50 minutes, of digestion were transferred into another conical tube and enzyme activity was stopped with equal volume of growth medium: MCDB+dexamethasone, (0.39 µg/ml)+epidermal growth factor (EGF) (10 ng/ml)+15% fetal bovine serum (FBS). Undigested tissue in the digestion tube was washed several times with growth medium and added to the cell harvest. Cells were spun down, resuspended in 2 ml of growth medium for the cell count and then, depending on cell density, seeded into 100 mm tissue culture dishes at approximately $3 \times 10^5$ cells/dish. Forty-eight to seventy-two hour cultures were frozen in growth medium and 10% DMSO at $2 \times 10^6$/ml to serve as a stock.

The fetal pig cardiomyocytes have an average doubling time of forty hours and generally complete about six doublings before they stop dividing. After about six doublings, the fetal pig cardiomyocytes continue to survive in culture for an long periods of time, e.g., months. When the fetal porcine cardiomyocytes are shifted to DMEM+10% horse serum after proliferation in MCDB, they contract synchronously for extended periods of time (e.g., greater than three weeks). A fetal pig heart typically yields approximately $1 \times 10^5$ cardiomyocytes. A superovulated pregnant pig, on average, gives birth to about 15–20 fetuses. A litter of fetuses, therefore, can yield at least about $1.2 \times 10^6$ cardiomyocytes per isolation.

To confirm that cardiomyocytes, which stain positive for the cardiac-specific marker, cardiac troponin (Scripps Labs, San Diego, Calif.), had been isolated, a FACS analysis was performed. For FACS analysis, 1×10$^5$ cells were first incubated at 4° C. in 100 μl of PBS with 1 μg of a primary mouse monoclonal antibody to cardiac troponin (Scripps Labs, CA) for 1 hour. Cells were washed three times with 1 ml of PBS and then incubated for 1 hour in 100 μl of PBS with 1 μg of a goat anti-mouse fluorescein conjugated secondary antibody (Cappel, Durham, N.C.) at 4° C. Cells were then washed three times with 1 ml of PBS, resuspended in 1 ml of PBS and subjected to FACS analysis using a Becton-Dickinson FACScan with Lysys II software for data analysis. The results of this analysis are illustrated in FIGS. 1A (control) (cardiomyocytes incubated with secondary antibody only) and 1B (cardiomyocytes incubated with both primary and secondary antibodies). Essentially all isolated cells stained positive for the cardiac-specific marker, cardiac troponin.

The isolated fetal pig cardiomyocytes were also subjected to immunofluorescence analysis as follows. The cardiomyocytes were grown on glass coverslips and then fixed in 4% paraformaldehyde. The cardiomyocytes were then washed free of paraformaldehyde and incubated in blocking buffer (PBS+1% goat serum+0.05% Tween-20) for thirty minutes at room temperature. Blocking buffer was then removed and replaced with a primary mouse monoclonal antibody to cardiac troponin (Scripps Labs, CA) diluted to 10 μg/ml in blocking buffer. The cardiomyocytes were incubated with the cardiac troponin antibody for 1 hour then washed in blocking buffer and incubated with secondary goat-anti-mouse fluorescein conjugated antibody diluted to 1 μg/ml in blocking buffer. The cardiomyocytes were incubated with secondary antibody for 1 hour and then washed in blocking buffer. Coverslips containing stained cardiomyocytes were mounted on glass slides and observed in a microscope equipped for fluorescence. There was weak staining of all isolated cells, indicating that the cells are cardiac derived and are not endothelial cells. However, within this population is the >20% (depends on the isolation, but can range from 20–60%) which show strong periodic staining of muscle myofibrils. Striated myofibrils do not appear until cells have become post-mitotic and have terminally differentiated. Therefore, the cells with strong periodic staining of myofibrils represent the mature cardiomyocytes in the population and the weaker staining cells the immature dividing population.

Example II
Transplantation of Fetal Pig Cardiomyocytes into Xenogeneic Recipients and Demonstration of Fetal Pig Cardiomyocyte Survival In Vivo For transplantation of the fetal cardiomyocytes into mice, the cardiomyocytes were injected directly into the ventricular myocardium of B6D2/F1 mice (Jackson Laboratories, Bar Harbor, Me.) (Soonpaa, M. H. et al. (1994) *Science* 264:98–101; Koh, G. Y. et al. (1993) *Am. J. Physiol.* 33:H1727–1733) using open heart surgery as described in Rockman, H. A. (1991) *Proc. Natl. Acad. Sci. USA* 88:8277–8281. Cardiomyocytes (4–10×10$^4$ from approximately 3–5 fetal pigs) were injected in a volume of 2–3 μl using a plastic syringe fitted with a 30-gauge needle. Cyclosporin (10–50 mg/kg) was administered to the mice beginning one day prior to transplantation. Ten recipient mice were sacrificed one month posttransplantation. The hearts of the mice were removed and examined for the presence of pig cardiomyocytes by in situ hybridization to a pig-specific repetitive DNA element (PRE) as described Oettinger, H. F. et al. (1995) *Cell Transplantation* 4(2):253–256. Hybridization using the PRE demonstrated that the fetal pig cardiomyocytes were present in the mice and had survived during the one month transplantation period.

Example III
Transplantation of Modified ("Masked") Fetal Pig Cardiomyocytes into Xenogeneic Recipients and Demonstration of Cardiomyocyte Survival In Vivo To demonstrate that porcine cardiomyocytes which are modified by binding antiMHC class I antibodies to the MHC class I antigens on their surface survive in a xenogeneic subject, porcine cardiomyocytes were incubated with F(ab')$_2$ fragments of PT-85, a mouse monoclonal antibody specific for porcine MHC class I. This incubation was performed in PBS for 1 hour at 4° C. with 1 μg antibody/10$^6$ cells. The cardiomyocytes having these antibodies bound to their MHC class I surface antigens are referred to hereinafter as "masked" cardiomyocytes. Control cells (unmasked) were incubated for the same time period in PBS. Prior to transplantation the cells were washed in Hanks solution at 4° C. to remove unbound antibody, and control cells were treated in the same way. The control cells were transplanted into mice as described in Example II except that the mice did not receive cyclosporin treatment.

Figure 2:
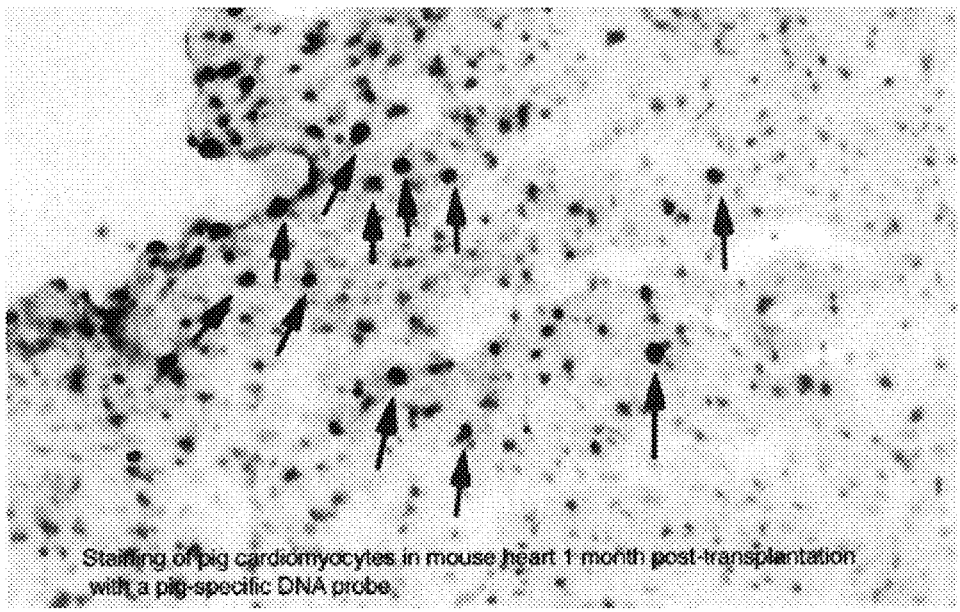
FIG. 2 is a photograph showing in situ hybridization to a pig-specific repetitive DNA element in pig cardiomyocytes transplanted into mouse heart.

Masked cardiomyocytes (4–10×10$^4$ from approximately 3–5 fetal pigs) were transplanted into ten mice as described in Example II. Cyclosporin (10–50 mg/kg) was administered to the mice beginning one day prior to transplantation. The ten recipient mice were sacrificed one month post-transplantation. The hearts of the mice were removed and examined for the presence of pig cardiomyocytes by in situ hybridization to a pig-specific repetitive DNA element (PRE) as described Oettinger, H. F. et al. (1995) *Cell Transplantation* 4(2):253–256. Hybridization was seen using the PRE and a representative image is shown in FIG. 2. As illustrated in FIG. 2, the porcine cardiomyocytes showed staining over the nucleus and several positive nuclei are highlighted by arrows.

Example IV
Methods of Detecting Pathogens in Swine

A. Collecting, Processing, and Analyzing Pig Fecal Samples for Signs of Pathogens Feces are extracted from the pig's rectum manually and placed in a sterile container. About a 1.5 cm diameter portion of the specimen was mixed thoroughly in 10 ml of 0.85% saline. The mixture is then strained slowly through a wire mesh strainer into a 15 ml conical centrifuge tube and centrifuged at 650×g for 2 minutes to sediment the remaining fecal material. The supernatant is decanted carefully so as not to dislodge the sediment and 10% buffered formalin was added to the 9 ml mark, followed by thorough mixing. The mixture is allowed to stand for 5 minutes. 4 ml of ethyl acetate is added to the mixture and the mixture is capped and mixed vigorously in an inverted position for 30 seconds. The cap is then removed to allow for ventilation and then replaced. The mixture is centrifuged at 500×g for 1 minute (four layers should result: ethyl acetate, debris plug, formalin and sediment). The debris plug is rimmed using an applicator stick. The top three layers are carefully discarded by pouring them off into a solvent container. The debris attached to the sides of the tube is removed using a cotton applicator swab. The sediment is mixed in either a drop of formalin or the small amount of formalin which remains in the tube after decanting. Two separate drops are placed on a slide to which a drop of Lugol's iodine is added. Both drops are coverslipped and carefully examined for signs of pathogens, e.g., protozoan cysts of trophozoites, helminth eggs and larvae. Protozoan cyst identification is confirmed, when required, by trichrome staining.

B. Co-cultivation Assay for Detecting the Presence of Human and Animal Viruses in Pig Cells Materials

Cell Lines

African green monkey kidney, (VERO), cell line American Type Culture Collection, (ATCC CCL81), human embryonic lung fibroblasts, (MRC-5) cell line American Type Culture Collection, (ATCC CCL 171), porcine kidney, (PK-15), cell line American Type Culture Collection, (ATCC CRL 33), porcine fetal testis, (ST), cell line American Type Culture Collection, (ATCC CRL 1746).

Medium, Antibiotics, and Other Cells and Equipment

Fetal calf serum, DMEM, Penicillin 10,000 units/ml, Streptomycin 10 mg/ml, Gentamicin 50 mg/ml, guinea pig erythrocytes, chicken erythrocytes, porcine erythrocytes, Negative Control (sterile cell culture medium), Positive Controls: VERO and MRC-5 Cells: Poliovirus type 1 attenuated, (ATCC VR-1 92) and Measles virus, Edmonston strain, (ATCC VR-24), PK-1 5 and ST Cells: Swine influenza type A, (ATCC VR-99), Porcine Parvovirus, (ATCC VR-742), and Transmissible gastroenteritis of swine, (ATCC VR-743). Equipment: tissue Culture Incubator, Inverted Microscope, Biological Safety Cabinet.

These materials can be used in a co-cultivation assay (a process whereby a test article is inoculated into cell lines (VERO, MRC-5, PKI 5, and ST) capable of detecting a broad range of human, porcine and other animal viruses). Hsuing, G. D., "Points to Consider in the Characterization of Cell Lines Used to Produce Biologicals" in Diagnostic Virology, 1982 (Yale University Press, New Haven, Conn., 1982).

Experimental Design and Methodology

A total of three flasks (T25) of each cell line are inoculated with at least 1 ml of test article. Three flasks of each cell line can also be inoculated with the appropriate sterile cell culture medium as a negative control. Positive control viruses are inoculated into three flasks of each cell line. After an absorption period, the inoculate is removed and all flasks incubated at 35–37° C. for 21 days. All flasks are observed at least three times per week for the development of cytopathic effects, (CPE), of viral origin. Harvests are made from any flasks inoculated with the test article that show viral CPE.

At Day 7 an aliquot of supernatant and cells from the flasks of each test article are collected and at least 1 ml is inoculated into each of three new flasks of each cell line. These subcultures are incubated at 35–37° C. for at least 14 days. All flasks are observed and tested as described above.

At Day 7, the flasks from each test article are also tested for viral hemadsorption, (HAd), using guinea pig, monkey and chicken erythrocytes at 2–8° C. and 35–37° C. at 14 days postinoculation.

At Day 21, if no CPE is noted, an aliquot of supernatant from each flask is collected, pooled, and tested for viral hemagglutination, (HA), using guinea pig, monkey, and chicken erythrocytes at 2–8° C. and 35–37° C. Viral identification is based on characteristic viral cytopathic effects (CPE) and reactivity in HA HAd testing.

The test samples are observed for viral cytopathic effects in the following manner: All cultures are observed for viral CPE at least three times each week for a minimum of 21 days incubation. Cultures are removed from the incubator and observed using an inverted microscope using at least 40× magnification. 100× or 200× magnification is used as appropriate. If any abnormalities in the cell monolayers, including viral CPE, are noted or any test articles cause total destruction of the cell monolayer, supernatant and cells are collected from the flasks and samples are subcultured in additional flasks of the same cell line. Samples can be stored at –60° to –80° C. until subcultured. After 7 and 14 days incubation, two blind passages are made of each test article by collecting supernatant and cells from all flasks inoculated with each sample. Samples can be stored at –600 to –80° C. until subcultured.

Hemadsorbing viruses are detected by the following procedure: after 21 days of incubation, a hemadsorption test is performed to detect the presence of hemadsorbing viruses. Supernatant fluids are collected and pooled from each flask inoculated with test articles or controls. Fluids are tested using guinea pig, monkey, and chicken erythrocytes. Hemagglutination testing is also performed after 21 days of incubation of the subcultures. Viral isolates are identified based on the cell line where growth was noted, the characteristics of the viral CPE, the hemadsorption reaction, and hemagglutination reactions, as appropriate. The test article is considered negative for the presence of a viral agent, if any of the cell lines used in the study demonstrate viral, CPE, HA, or HAd in a valid assay.

C. Procedure for Preparing and Maintaining Cell Lines Used to Detect Viruses in Pig Cells Materials Fetal calf serum (FCS), DMEM, Penicillin 10,000 unit/ml, Streptomycin 10 mg/ml, Gentamicin 50 mg/ml, T25 tissue culture flasks, tissue culture incubator (5% $CO_2$, 37° C.)

Procedure

Aseptic techniques are followed when performing inoculations and transfers. All inoculations and transfers are performed in a biological safety cabinet. Media is prepared by adding 10% FCS for initial seeding, 5% FCS for maintenance of cultures, as well as 5.0 ml of penicillin/streptomycin and 0.5 ml of gentamicin per 500 ml media. Sufficient media is added to cover the bottom of a T25 tissue culture flask. The flask is seeded with the desired cell line and incubated at 37° C., 5% $CO_2$ until cells are 80 to 100% confluent. The flasks are then inoculated with virus (QCP25).

D. Preparation of Erythrocyte (rbc) Suspensions Used in Hemadsorption (HAd) and Hemagglutination (HA) Virus Detection Testing Materials Phosphate buffered saline, (PBS), pH 7.2, guinea pig erythrocytes stock solution, porcine erythrocytes stock solution, chicken erythrocytes stock solution, sterile, disposable centrifuge tubes, 15 or 50 ml Laboratory centrifuge Procedure An appropriate amount of erythrocytes (rbc) is obtained from stock solution. The erythrocytes are washed 3 times with PBS by centrifugation at approximately 1000×g for 10 minutes. A 10% suspension is prepared by adding 9 parts of PBS to each one part of packed erythrocytes. The 10% rcb suspensions are stored at 2–8° C. for no more than one week. 0.5% ecb suspensions are prepared by adding 19 parts of PBS to each one part of 10% rbc suspension. Fresh 0 5% rbc suspensions are prepared prior to each day's testing.

Hemagglutination (HA) Test

A hemagglutination test is a test that detects viruses with the property to agglutinate erythrocytes, such as swine influenza type A, parainfluenza, and encephalomyocarditus viruses, in the test article. Hsuing, G. D. (1982) Diagnostic Virology (Yale University Press, New Haven, Conn.);. Stites, Daniel P and Terr, Abba I, (1991), Basic and Clinical Immunology (Appleton & Lange, East Norwalk, Conn.).

Materials

Supernatants from flasks of the VERO cell line, MRC-5 inoculated with the test article, flasks of positive and negative controls, phosphate buffered saline (PBS), pH 7.2, guinea pig erythrocytes (GPRBC), 0.5% suspension in PBS, chicken erythrocytes (CRBC), 0.5% suspension in PBS, porcine erythrocytes (MRBC), 0.5% suspension in PBS Procedure All sample collection and testing is performed in an approved biological safety cabinet. 0.5% suspensions of each type of erythrocytes are prepared as described above. The HA test on all cell lines inoculated with samples of the test articles at least 14 days postinoculation. Positive and negative control cultures are included for each sample and monolayers are examined to ensure that they are intact prior to collecting samples.

At least 1 ml of culture fluid from each flask inoculated with the test article is collected and pooled. 1 ml samples from the negative and positive control cultures are also collected and pooled. A set of tubes is labeled with the sample number and type of erythrocyte (distinguish positive and negative suspension) to be added. Racks may be labeled to differentiate the type of erythrocyte. 0.1 ml of sample is added to each tube. 0.1 ml of the appropriate erythrocyte suspension is added to each tube. Each tube is covered with parafilm and mixed thoroughly. One set of tubes is incubated at 2–8° C. until tight buttons form in the negative control in about 30–60 minutes. Another set of tubes is incubated at 35–37° C. until tight buttons form in the negative control in about 30–60 minutes.

Formation of a tight button of erythrocytes indicates a negative result. A coating of the bottom of the tube with the erythrocytes indicates a positive result.

E. Methods Used for Fluorescent Antibody Stain of Cell Suspensions Obtained from flasks Used in Detection of Viruses in Porcine Cells Using Cell Culture Techniques (as Described in Sections B and C)

Materials

Pseudorabies, parvovirus, enterovirus. adenovirus, transmissible Gastroenteritis Virus. bovine viral diarrhea, encephalomyocarditus virus, parainfluenza, vesicular stomatitis virus., microscope slides, PBS, incubator with humidifying chamber at 36° C., Evan's blue coutner stain, DI Water, fluorescent microscope, trypsin, serum containing media, acetone, T25 Flask.

Procedure

Cells (described in Sections B and C) are trypsinized to detach them from the T25 flask and sufficient media is added to neutralize trypsin activity. A drop of cell suspension is placed on each microscope slide and allowed to air dry. A slide for each fluorescent antibody is prepared. Cells are fixed by immersion in acetone for five minutes. Each fluorescent antibody solution is placed on each slide to cover cells and the slides are incubated in humidifying chamber in incubator at 36° C. for 30 minutes. The slides are then washed in PBS for five minutes. The wash is repeated in fresh PBS for five minutes followed by a rinse with DI water.

The cells are counterstained by placing Evan's blue solution on each slide to cover cells for five minutes at room temperature. The slides are then washed in PBS for five minutes. The wash is repeated in fresh PBS for five minutes followed by a rinse with DI water. The slides are then allowed to air dry. Each slide is inspected under a fluorescent microscope. Any fluorescent inclusion bodies characteristic of infection are considered a positive result for the presence of virus.

F. Procedures for Defining Bacteremic Pigs Materials

Anaerobic BMB agar (5% sheep blood, vitamin K and hemin [BMB/blood]), chocolate Agar with Iso Vitalex, Sabaroud dextrose agar/Emmons, 70% isopropyl alcohol swabs, betadine solution, 5% $CO_2$ incubator at 35–37° C., anaerobic blood agar plate, gram stain reagents (Columbia Broth Media), aerobic blood culture media (anaerobic brain heart infusion with vitamin K & hemin), septicheck media system, vitek bacterial identification system, laminar flow hood, microscope, and bacteroids and Bacillus stocks Procedure Under a laminar flow hood, disinfect the tops of bottles for aerobic and anaerobic blood cultures of blood obtained from pig with 70% isopropyl alcohol, then with betadine The rubber stopper and cap from the aerobic blood culture bottle are removed and a renal septicheck media system is attached to the bottle. The bottles are incubated in 5% $CO_2$ for 21 days at 35–37° C., and observed daily for any signs of bacterial growth (i.e. gas bubbles, turbidity, discoloration or discrete clumps). Negative controls consisting of 5 cc of sterile saline in each bottle and positive controls consisting of Bacillus subtilis in the aerobic bottle and Bacteriodes Vulgaris in the anaerobic bottle are used. If signs of bacterial growth are observed, a Gram stain is prepared and viewed microscopically at 100× oil immersion for the presence of any bacteria or fungi. The positive bottles are then subcultured onto both chocolate agar plates with Iso Vitlex and onto BMB plates. The chocolate plate is incubated at 35–37° C. in 5% $CO_2$ for 24 hours and the BMB anaerobically at 35–37° C. for 48 hours. Any yeast or fungi that is in evidence at gram stain is subcultured onto a Sabaroud dextrose/Emmons plate. The Vitek automated system is used to identify bacteria and yeast. Fungi are identified via their macroscopic and microscopic characteristic. If no signs of growth are observed at the end of 21 days, gram stain is prepared and observed microscopically for the presence of bacteria and fungi.

Absence of growth in the negative control bottles and presence of growth in the positive control bottles indicates a valid test. The absence of any signs of growth in both the aerobic and anaerobic blood culture bottles, as well as no organisms seen on gram stain indicates a negative blood culture. The presence and identification of microorganism(s) in either the aerobic or anaerobic blood culture bottle indicates of a positive blood culture; this typically is due to a bacteremic state.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method for treating a disorder characterized by insufficient cardiac function in a human subject comprising: administering to the subject a composition comprising an isolated porcine cardiomyocyte obtained from an embryonic pig between about days 20–30 of gestation, wherein the cardiomyocytes or the subject are treated to reduce immune-mediated rejection of the cardiomyocytes, such that the disorder is treated.

2. The method of claim 1, wherein the subject has congestive heart failure.

3. The method of claim 1, wherein the subject has had a myocardial infarction.

4. A method for transplanting xenogeneic cardiomyocytes into a subject comprising: isolating porcine cardiomyocytes and introducing the porcine cardiomyocytes into a subject, wherein the cardiomyocytes or the subject are treated to reduce immune-mediated rejection of the cardiomyocytes, to thereby transplant xenogeneic cardiomyocytes into a subject.

5. The method of claim 4, wherein the porcine cardiomyocytes are obtained from an embryonic pig.

6. The method of claim 4, wherein the porcine cardiomyocytes are obtained from an embryonic pig between about days 20 and 30 of gestation.

7. The method of claim 4, wherein the xenogeneic subject is a human.

8. The method of claim 4, wherein the subject has congestive heart failure.

9. The method of claim 4, further comprising administering an immunosuppressive agent to the subject.

* * * * *